(12) United States Patent
Thomsen et al.

(10) Patent No.: US 10,538,797 B2
(45) Date of Patent: Jan. 21, 2020

(54) METHOD FOR THE BIOTECHNOLOGICAL PRODUCTION OF FLAVONE GLYCOSIDE DIHYDROCHALCONES

(71) Applicant: SYMRISE AG, Holzminden (DE)

(72) Inventors: Maren Thomsen, Greifswald (DE); Jakob Ley, Holzminden (DE); Egon Gross, Holzminden (DE); Winfried Hinrichs, Greifswald (DE); Uwe Bornscheuer, Greifswald (DE)

(73) Assignee: SYMRISE AG, Holzminden (DE)

( * ) Notice: Subject to any disclaimer, the term of this patent is extended or adjusted under 35 U.S.C. 154(b) by 16 days.

(21) Appl. No.: 15/322,768

(22) PCT Filed: Jun. 27, 2015

(86) PCT No.: PCT/EP2015/064626
§ 371 (c)(1),
(2) Date: Apr. 6, 2018

(87) PCT Pub. No.: WO2016/012198
PCT Pub. Date: Jan. 28, 2016

(65) Prior Publication Data
US 2018/0216152 A1 Aug. 2, 2018

(30) Foreign Application Priority Data
Jul. 1, 2014 (EP) .................................... 14175312

(51) Int. Cl.
*C12P 19/60* (2006.01)
*C12P 17/06* (2006.01)
*A23L 27/30* (2016.01)

(52) U.S. Cl.
CPC ............. *C12P 19/605* (2013.01); *A23L 27/33* (2016.08); *C12P 17/06* (2013.01); *C12Y 103/01031* (2013.01); *C12Y 505/01006* (2013.01)

(58) Field of Classification Search
None
See application file for complete search history.

(56) References Cited

U.S. PATENT DOCUMENTS

| 9,359,622 B2 * | 6/2016 | Hilmer ........... C12Y 505/01006 |
| 2014/0045233 A1 * | 2/2014 | Hilmer ........... C12Y 505/01006 435/148 |

FOREIGN PATENT DOCUMENTS

EP 2 692 729 A1 2/2014

OTHER PUBLICATIONS

Accession V9P0A9. Mar. 19, 2014. Alignment to SEQ ID No. 2 (Year: 2014).*
Accession V9P0A9. Mar. 19, 2014. Alignment to SEQ ID No. 4 (Year: 2014).*
Accession KF154734. Dec. 31, 2013. Alignment to SEQ ID No. 1. (Year: 2013).*
Accession KF154734. Dec. 31, 2013. Alignment to SEQ ID No. 3. (Year: 2013).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Bornscheuer et al. Curr Protoc Protein Sci. Nov. 2011;Chapter 26:Unit26.7. (Year: 2011).*
Gall et al, "Enzymatische Umsetzung von Flavonoiden mit einer backteriellen Chalconisomerase und einer Enoatreduktase," Angewandte Chemie vol. 126, No. 5, Jan. 27, 2014, pp. 1463-1466.

* cited by examiner

Primary Examiner — Christian L Fronda
(74) Attorney, Agent, or Firm — Polsinelli PC

(57) ABSTRACT

The invention relates to a method for producing flavone glycoside dihydrochalcones, having the following steps: (a) providing a transgenic microorganism containing (i) a first nucleic acid portion (A) containing a gene which codes for a bacterial chalcone isomerase and (ii) a second nucleic acid portion (B) containing a gene which codes for a bacterial enoate reductase, (b) adding one or more flavone glycosides to the transgenic microorganism under conditions which allow the simultaneous isomerization and reduction of the flavone glycoside into the flavone glycoside dihydrochalcone, and optionally (d) isolating and purifying the final product, wherein the nucleic acid portion (A) (1) is a nucleotide sequence according to SEQ ID NO:1, in which the nucleic acid portion (A') according to SEQ ID NO:3 has been cut out, or (2) is an amino acid sequence according to SEQ ID NO:2, in which the amino acid portion (A') according to SEQ ID NO:4 has been cut out.

12 Claims, 2 Drawing Sheets

Specification includes a Sequence Listing.

Plasmide pET28_CHI_ΔLid.

SDS-PAGE of the expression of the double transformation of pET22_ERED and pET28_CHI_ΔLid. 0h denotes the time point of the induction.

Conversion of the substrates by means of whole-cell-catalysis.

SEQUENCE LISTING

```
<160> NUMBER OF SEQ ID NOS: 9

<210> SEQ ID NO 1
<211> LENGTH: 852
<212> TYPE: DNA
<213> ORGANISM: Eubacterium ramulus

<400> SEQUENCE: 1
atggcagatt tcaaattcga accaatgaga agtcttatct acgttgactg cgtaagcgaa      60
gactacagac caaaacttca gagatggatt tataaagtac atattccgga cagcatctct     120
cagtttgagc cgtatgttac caaatatgca ttttatccgt ccttcccgat tccaccacag     180
ggtgatcgtt tcggatacgc aagaatgcag ctgacagagc atcactggtt agtaagcgac     240
cttgatcctc gtcttgagat caaagcaatc gctgagacat tcccgatgga cgtacttgta     300
tggcagggac agatcccggc agcagctcat acagacgctc agatcgattc tgacggagat     360
gcaggaaatg cagcccgtaa atccaacaat gcagaaggaa atccatttat ctttgcattc     420
cttccgatgt ggtgggagaa agacctgaaa ggaaaaggac gtacgatcga ggacggcgca     480
aactatcgtt tcaatatgac tatcggtttc ccagaaggcg tagacaaagc agagggagag     540
aaatggttat ttgagaaagt agttccgatt cttcaggcag ctccggagtg tacacgtgta     600
cttgcaagtg ccgtaaagaa agacatcaac ggatgcgtaa tggattgggt acttgaaatc     660
tggtttgaga atcagtccgg atggtacaaa gtaatggtag atgacatgaa agcacttgaa     720
aaaccgtcat gggctcagca ggatgctttc ccgttcctga aaccataccaa caatgtttgc    780 agtgcagcag ttgctgatta taccaagca aacaaccttg caattatcg tggatacatc     840 accatgagat aa                                                          852

<210> SEQ ID NO 2
<211> LENGTH: 283
<212> TYPE: PRT
<213> ORGANISM: Eubacterium ramulus

<400> SEQUENCE: 2

Met Ala Asp Phe Lys Phe Glu Pro Met Arg Ser Leu Ile Tyr Val Asp
1               5                   10                  15

Cys Val Ser Glu Asp Tyr Arg Pro Lys Leu Gln Arg Trp Ile Tyr Lys
                20                  25                  30

Val His Ile Pro Asp Ser Ile Ser Gln Phe Glu Pro Tyr Val Thr Lys
            35                  40                  45

Tyr Ala Phe Tyr Pro Ser Phe Pro Ile Pro Pro Gln Gly Asp Arg Phe
        50                  55                  60
```

```
Gly Tyr Ala Arg Met Gln Leu Thr Glu His His Trp Leu Val Ser Asp
 65                  70                  75                  80

Leu Asp Pro Arg Leu Glu Ile Lys Ala Ile Ala Glu Thr Phe Pro Met
                 85                  90                  95

Asp Val Leu Val Trp Gln Gly Gln Ile Pro Ala Ala His Thr Asp
            100                 105                 110

Ala Gln Ile Asp Ser Asp Gly Asp Ala Gly Asn Ala Ala Arg Lys Ser
            115                 120                 125

Asn Asn Ala Glu Gly Asn Pro Phe Ile Phe Ala Phe Leu Pro Met Trp
130                 135                 140

Trp Glu Lys Asp Leu Lys Gly Lys Gly Arg Thr Ile Glu Asp Gly Ala
145                 150                 155                 160

Asn Tyr Arg Phe Asn Met Thr Ile Gly Phe Pro Glu Gly Val Asp Lys
                165                 170                 175

Ala Glu Gly Glu Lys Trp Leu Phe Glu Lys Val Val Pro Ile Leu Gln
            180                 185                 190

Ala Ala Pro Glu Cys Thr Arg Val Leu Ala Ser Ala Val Lys Lys Asp
            195                 200                 205

Ile Asn Gly Cys Val Met Asp Trp Val Leu Glu Ile Trp Phe Glu Asn
210                 215                 220

Gln Ser Gly Trp Tyr Lys Val Met Val Asp Asp Met Lys Ala Leu Glu
225                 230                 235                 240

Lys Pro Ser Trp Ala Gln Gln Asp Ala Phe Pro Phe Leu Lys Pro Tyr
                245                 250                 255

His Asn Val Cys Ser Ala Ala Val Ala Asp Tyr Thr Pro Ser Asn Asn
            260                 265                 270

Leu Ala Asn Tyr Arg Gly Tyr Ile Thr Met Arg
            275                 280

<210> SEQ ID NO 3
<211> LENGTH: 66
<212> TYPE: DNA
<213> ORGANISM: Eubacterium ramulus

<400> SEQUENCE: 3
catacagacg ctcagatcga ttctgacgga gatgcaggaa atgcagcccg taaatccaac    60
aatgca                                                              66

<210> SEQ ID NO 4
<211> LENGTH: 22
<212> TYPE: PRT
<213> ORGANISM: Eubacterium ramulus

<400> SEQUENCE: 4

His Thr Asp Ala Gln Ile Asp Ser Asp Gly Asp Ala Gly Asn Ala Ala
  1               5                  10                  15

Arg Lys Ser Asn Asn Ala
             20

<210> SEQ ID NO 5
<211> LENGTH: 2037
<212> TYPE: DNA
<213> ORGANISM: Eubacterium ramulus

<400> SEQUENCE: 5
atggcagaaa aaaatcagta ttttccacat ttgtttgagc cgttaaaagt tggttcaaag    60
```

```
acaattaaga accgtattga ggcagcaccg gctttatttg cattcgagca ttatatcgaa    120
ctgaatccgg atccgtttgg ctataccaca ccggttccgg agcgtgcgtt ccgtatgctg    180
gaggcaaagg caaaaggagg ggcaggaatt gtatgtctgg gtgagttaag cccgaatcat    240
gagtatgaca acggtttcc gtttgaaccg tatcttgatt ttacatccag atcagataag    300
cagtttgaaa ttatgaagga aactgcggag atgatcaaaa gctatggggc atttccgatg    360
ggcgagctgc tttcctgcgg tgaaatcaag acaaatatcg gagatggtat caatccgaag    420
ggaccatctg agaaagatct tccggatggc tctcatgtgg aggcgtttac aaaagaagag    480
attttaagct gctatcagga ttatgtaact gcatgtaaat ggtttcaggc agcaggctgg    540
gaaggcatta tgatccactg cggacatggc tggcttccgg cacagttcct gtctccgcaa    600
tacaataaac gtaccgatga gtatggtgga tcttttgaaa acagagcaag atttactgtt    660
gatctgttaa aaactgttcg tgaagctatg ggaccggact tcgtgatcga gatccgtgtc    720
agcagctctg agcatttacc gggcggatta gagctggaag atgctgtaaa ttattgtaaa    780
ctgtgtgagc catacattga tatgatccat gtctcctgtg gtcattacct gagttcttcc    840
agaagttggg agttcacaac tgcttatgca ccgcatggtc cgaatattga accggcagct    900
gttatcaaac agaacgtatc cattccggtt gcggcagtcg gcggcatcaa ttctccggaa    960
caggcggaag aggcaatcgc gtcaggaaaa atcgatatgg tatccatggg acgtcagttc   1020
tttgcagatc cggcatttcc aaacaaggca aagaagggc atgcagatga gatccgtcgc   1080
tgtctgcgct gcggaagatg ctatccgggt ccgtccggcg agcatgaaac agagatctgg   1140
acggtgaaat tcccaccact ggattcctgt accatcaatc catatgatgt atggccggca   1200
tctcatcata aagtccttcc ggaccgcatg ccgaaaccgg aagcaagccg taaggtattg   1260
gtagtaggcg gcggctgtgg cggtctgcag acagcgatca cagcatcaga cagaggtcat   1320
caggtaatcc tgtgcgaaaa atccggagta ttaggcggtc tgatcaattt tacggatcat   1380
acggatcata aagtagatat cagaaacttc aaagatctgc tgatccgcga tgtggagaaa   1440
cgtccgatcg aagtaagatt aaactgtgaa gtaacaccgg aactcatcag agaaattgct   1500
ccggaagcag ttgtactggc cgtcggatcc gatgatctga tccttccaat cgagggaatt   1560
gaaaatgcgg taacagcaat ggacgtatac agcaatgact ttgcaggtct tggaaagagc   1620
accatcgtac tcggtggcgg tctggttggc tgtgaggcag ccgcagatta tattgatcac   1680
ggtgtagaga caacgattgt tgaaatgaaa ggtgcgctga tgccggagac aaccggtctg   1740
taccgtacag ctgtacatga tttcatcgac aaaaacggcg gcaaatacga agtaaatgca   1800
aaagttgtca agttggcaa agattttgtg gtagcggaac aagatgggaa agagattacc   1860
atcaaagcag attctgttgt caatgcaatg ggacgccgtg cgcatgcgac agaagcactt   1920
gagacagcta tcaaagaagc tggtattccg gtatggaaga tcggtgactg tgtccgtgcg   1980
cgtcagatcg gtgatgcggt aagagaaggc tggaccgcag caatggaaat tatctaa     2037
```

<210> SEQ ID NO 6
<211> LENGTH: 678
<212> TYPE: PRT
<213> ORGANISM: Eubacterium ramulus

<400> SEQUENCE: 6

Met Ala Glu Lys Asn Gln Tyr Phe Pro His Leu Phe Glu Pro Leu Lys
1               5                   10                  15

Val Gly Ser Lys Thr Ile Lys Asn Arg Ile Glu Ala Ala Pro Ala Leu
            20                  25                  30

-continued

Phe Ala Phe Glu His Tyr Ile Glu Leu Asn Pro Asp Pro Phe Gly Tyr
        35                  40                  45

Thr Thr Pro Val Pro Glu Arg Ala Phe Arg Met Leu Glu Ala Lys Ala
    50                  55                  60

Lys Gly Ala Gly Ile Val Cys Leu Gly Glu Leu Ser Pro Asn His
65              70                  75                  80

Glu Tyr Asp Lys Arg Phe Pro Phe Glu Pro Tyr Leu Asp Phe Thr Ser
                85                  90                  95

Arg Ser Asp Lys Gln Phe Glu Ile Met Lys Glu Thr Ala Glu Met Ile
                100                 105                 110

Lys Ser Tyr Gly Ala Phe Pro Met Gly Glu Leu Leu Ser Cys Gly Glu
        115                 120                 125

Ile Lys Thr Asn Ile Gly Asp Gly Ile Asn Pro Lys Gly Pro Ser Glu
        130                 135                 140

Lys Asp Leu Pro Asp Gly Ser His Val Glu Ala Phe Thr Lys Glu Glu
145                 150                 155                 160

Ile Leu Ser Cys Tyr Gln Asp Tyr Val Thr Ala Cys Lys Trp Phe Gln
                165                 170                 175

Ala Ala Gly Trp Glu Gly Ile Met Ile His Cys Gly His Gly Trp Leu
            180                 185                 190

Pro Ala Gln Phe Leu Ser Pro Gln Tyr Asn Lys Arg Thr Asp Glu Tyr
            195                 200                 205

Gly Gly Ser Phe Glu Asn Arg Ala Arg Phe Thr Val Asp Leu Leu Lys
        210                 215                 220

Thr Val Arg Glu Ala Met Gly Pro Asp Phe Val Ile Glu Ile Arg Val
225                 230                 235                 240

Ser Ser Ser Glu His Leu Pro Gly Gly Leu Glu Leu Gly Asp Ala Val
                245                 250                 255

Asn Tyr Cys Lys Leu Cys Glu Pro Tyr Ile Asp Met Ile His Val Ser
            260                 265                 270

Cys Gly His Tyr Leu Ser Ser Arg Ser Trp Glu Phe Thr Thr Ala
        275                 280                 285

Tyr Ala Pro His Gly Pro Asn Ile Glu Pro Ala Ala Val Ile Lys Gln
        290                 295                 300

Asn Val Ser Ile Pro Val Ala Ala Val Gly Gly Ile Asn Ser Pro Glu
305                 310                 315                 320

Gln Ala Glu Glu Ala Ile Ala Ser Gly Lys Ile Asp Met Val Ser Met
                325                 330                 335

Gly Arg Gln Phe Phe Ala Asp Pro Ala Phe Pro Asn Lys Ala Lys Glu
            340                 345                 350

Gly His Ala Asp Glu Ile Arg Arg Cys Leu Arg Cys Gly Arg Cys Tyr
        355                 360                 365

Pro Gly Pro Ser Gly Glu His Glu Thr Glu Ile Trp Thr Val Lys Phe
    370                 375                 380

Pro Pro Leu Asp Ser Cys Thr Ile Asn Pro Tyr Asp Val Trp Pro Ala
385                 390                 395                 400

Ser His His Lys Val Leu Pro Asp Arg Met Pro Lys Pro Glu Ala Ser
                405                 410                 415

Arg Lys Val Leu Val Val Gly Gly Cys Gly Gly Leu Gln Thr Ala
            420                 425                 430

Ile Thr Ala Ser Asp Arg Gly His Gln Val Ile Leu Cys Glu Lys Ser
        435                 440                 445

Gly Val Leu Gly Gly Leu Ile Asn Phe Thr Asp His Thr Asp His Lys
        450                 455                 460

Val Asp Ile Arg Asn Phe Lys Asp Leu Leu Ile Arg Asp Val Glu Lys
465                 470                 475                 480

Arg Pro Ile Glu Val Arg Leu Asn Cys Glu Val Thr Pro Glu Leu Ile
                485                 490                 495

Arg Glu Ile Ala Pro Glu Ala Val Leu Ala Val Gly Ser Asp Asp
            500                 505                 510

Leu Ile Leu Pro Ile Glu Gly Ile Glu Asn Ala Val Thr Ala Met Asp
        515                 520                 525

Val Tyr Ser Asn Asp Phe Ala Gly Leu Gly Lys Ser Thr Ile Val Leu
530                 535                 540

Gly Gly Gly Leu Val Gly Cys Glu Ala Ala Ala Asp Tyr Ile Asp His
545                 550                 555                 560

Gly Val Glu Thr Thr Ile Val Glu Met Lys Gly Ala Leu Met Pro Glu
                565                 570                 575

Thr Thr Gly Leu Tyr Arg Thr Ala Val His Asp Phe Ile Asp Lys Asn
            580                 585                 590

Gly Gly Lys Tyr Glu Val Asn Ala Lys Val Lys Val Gly Lys Asp
        595                 600                 605

Phe Val Val Ala Glu Gln Asp Gly Lys Glu Ile Thr Ile Lys Ala Asp
610                 615                 620

Ser Val Val Asn Ala Met Gly Arg Arg Ala His Ala Thr Glu Ala Leu
625                 630                 635                 640

Glu Thr Ala Ile Lys Glu Ala Gly Ile Pro Val Trp Lys Ile Gly Asp
                645                 650                 655

Cys Val Arg Ala Arg Gln Ile Gly Asp Ala Val Arg Glu Gly Trp Thr
            660                 665                 670

Ala Ala Met Glu Ile Ile
        675

<210> SEQ ID NO 7
<211> LENGTH: 2037
<212> TYPE: DNA
<213> ORGANISM: Eubacterium ramulus

<400> SEQUENCE: 7
atggcagaaa agaaccaata cttcccgcac ctgtttgaac cgctgaaagt cggctctaaa      60
accattaaaa atcgcatcga agcagcaccg ccctgtttg cattcgaaca ttatatcgaa      120
ctgaacccgg accgtttgg ttacaccacg ccggtgccgg aacgtgcatt ccgtatgctg      180
gaagccaaag caaaggcgg tgccggcatt gtttgtctgg gtgaactgag cccgaatcac      240
gaatatgata aacgctttcc gttcgaaccg tacctggatt ttaccagccg ttctgacaaa      300
cagttcgaaa ttatgaaaga acggcagaa atgatcaaaa gctatggcgc ttttccgatg      360
ggtgaactgc tgtcgtgcgg tgaaatcaaa accaacattg cgatggtat caatccgaaa      420 ggcccgtcag aaaaagatct gccggacggt tcgcatgtgg aagccttcac caaagaagaa      480
atcctgtcat gttaccagga ttacgttacg gcatgcaaat ggttccaagc ggccggctgg      540
gaaggtatta tgatccattg tggccacggt tggctgccgg cgcagtttct gagcccgcaa      600
tataacaaac gcaccgatga atacggcggt tcttttgaaa atcgtgcgcg cttcaccgtc      660
gatctgctga aaacggtgcg tgaagcgatg gccccgact tcgtgattga aatccgtgtt      720
agctctagtg aacatctgcc gggcggtctg gaactggaag atgcggtgaa ctattgcaaa      780

```
ctgtgtgaac cgtacattga catgatccat gttagttgcg gccactatct gtcctcatcg    840
cgctcctggg aatttaccac ggcttacgcg ccgcacggtc cgaacatcga accggcagct    900
gtcattaaac agaatgtgag catcccggtt gcagcagtcg gcggtatcaa ctctccggaa    960
caagcggaag aagccattgc aagtggcaaa atcgatatgg ttagcatggg ccgtcagttt   1020
ttcgctgacc cggcgtttcc gaataaagca aaagaaggcc atgctgatga aattcgtcgc   1080
tgcctgcgtt gtggtcgctg ctatccgggc ccgagtggtg aacacgaaac cgaaatctgg   1140
acggtgaaat tcccgccgct ggatagttgt accattaacc cgtacgacgt gtggccggca   1200
tcccatcaca aagttctgcc ggatcgcatg ccgaaaccgg aagcgtcccg taaagttctg   1260
gtggttggcg gtggctgtgg tggtctgcag accgcaatca cggcatcaga ccgcggccat   1320
caagtcattc tgtgcgaaaa atcgggtgtg ctgggtggcc tgattaactt taccgatcat   1380
acggaccaca aagttgatat tcgcaatttc aaagatctgc tgatccgtga cgtcgaaaaa   1440
cgcccgattg aagttcgtct gaattgtgaa gtcaccccgg aactgattcg tgaaatcgct   1500
ccggaagcag tcgtgctggc agtgggcagt gatgacctga ttctgccgat cgaaggtatt   1560
gaaaacgccg ttaccgcaat ggatgtctat agcaatgact ttgccggcct gggtaaatct   1620
acgatcgtgc tgggtggcgg tctggttggc tgcgaagcag ctgcggatta tatcgatcat   1680
ggcgtggaaa ccacgattgt tgaaatgaaa ggcgcactga tgccggaaac cacgggtctg   1740
tatcgtaccg ctgtgcacga ttttattgac aaaaacggcg gtaaatacga agtcaatgcc   1800
aaagttgtca aagtgggcaa agatttcgtg gttgcagaac aggacggtaa agaaattacc   1860
atcaaagcgg attctgtcgt gaatgcgatg ggccgtcgcg ctcacgcaac cgaagctctg   1920
gaaacggcga ttaaagaagc cggcatcccg gtttggaaaa ttggtgattg cgtccgtgcc   1980
cgccaaatcg gtgacgcagt tcgtgaaggc tggacggctg caatggaaat catctaa     2037

<210> SEQ ID NO 8
<211> LENGTH: 27
<212> TYPE: DNA
<213> ORGANISM: Eubacterium ramulus
<220> FEATURE:
<223> OTHER INFORMATION: Forward primer

<400> SEQUENCE: 8
gatcccggca gcagcagaag gaaatcc                                         27

<210> SEQ ID NO 9
<211> LENGTH: 27
<212> TYPE: DNA
<213> ORGANISM: Eubacterium ramulus
<220> FEATURE:
<223> OTHER INFORMATION: Reverse Primer

<400> SEQUENCE: 9
ggatttcctt ctgctgctgc cgggatc                                         27
```

METHOD FOR THE BIOTECHNOLOGICAL PRODUCTION OF FLAVONE GLYCOSIDE DIHYDROCHALCONES

CROSS-REFERENCE TO RELATED APPLICATIONS

This application is a national stage application (under 35 U.S.C. § 371) of PCT/EP2015/064626, filed Jun. 27, 2015, which claims benefit of European Application No. 14175312.9, filed Jul. 1, 2014, which are incorporated herein by reference in their entireties.

FIELD OF THE INVENTION

The invention is in the field of biotechnology and relates to a method in which flavanone glycosides are converted without chemical intermediate steps to the corresponding dihydrochalcones and to a corresponding microorganism, a vector and a host cell.

PRIOR ART

As part of a research program of the US Department of Agriculture to reduce the bitter taste in citrus juices, in the mid 1960s a number of flavanone glycosides such as naringin, hesperidin and narirutin were recognised as the crucial bitter substances. Furthermore, it was found that the hydrogenation of the flavanone glycosides to dihydrochalcones leads to substances that taste up to 1800 times sweeter than sugar at the detection limit of the sweetening effect; if sugar is exchanged for these dihydrochalcones in a weight ratio of 1:1, the dihydrochalcones still prove to be more efficient by at least a factor of 300. Naringin dihydrochalcone, hesperidin dihydrochalcone and neohesperidin dihydrochalcone are currently not only among the most powerful sweeteners, but are also useful in particular to mask the bitter taste of citrus substances.

Certain dihydrochalcone glycosides can be obtained by extraction from berries, especially from *Malus* spp. However, the process is complicated, expensive and also depends on the season, and is therefore technically unimportant.

Starting from flavanone glycosides the production of dihydrochalcones is nowadays performed by catalytic reduction under strongly basic conditions or by a Friedel-Crafts type acylation of phenols with dihydrocinnamic acids. Even though the synthesis is carried out in satisfactory yields and is industrially established, it has one major disadvantage however: it is a chemical manufacturing process, which means that for regulatory reasons the final product cannot be declared natural.

In this context, it is referred to the following documents in prior art:

EP 2692729 A1 (SYMRISE) discloses a process for producing a dihydrochalcone using a transgenic microorganism, comprising the following steps: Providing a transgenic microorganism containing a nucleic acid section (a) comprising or consisting of a gene coding for a bacterial chalcone isomerase, and/or a nucleic acid section (a'), comprising or consisting of a gene coding for a plant chalcone isomerase, and also a nucleic acid section (b) comprising or consisting of a gene coding for a bacterial enoate reductase, addition of one or more flavanones, and/or one or more precursors or one or more derivatives thereof, to the transgenic microorganism and culturing the transgenic microorganism under conditions that permit the conversion of the flavanone or flavanones and/or the precursor(s) or the derivative or derivatives thereof to a dihydrochalcone, as well as optionally: isolating and optionally purifying the dihydrochalcone, in particular phloretin.

The paper by Gall et al. having the title "*Enzymatic conversion of flavonoids with a bacterial chalcone isomerase and an enoate reductase*" (Angewandte Chemie, 2014, 126 (5), pp. 1463-1466) describes the identification and the recombinant expression of chalcone isomerase and an enoate reductase from the anaerobic bacterium *Eubacterium ramulus*. The *E. coli* strain expressing the two enzymes can be used to carry out the conversion of various flavanones to their respective dihydrochalcones.

Content of US 2013/0136839 (NUTRINOVA) is a composition of sweetening substances, including a sweetener and at least one taste masking substance. Among the possible and various taste masking substances which can be used, naringin dihydrochalcone is found.

EP 2529633 A1 (SYMRISE) finally describes an oral edible composition, which can comprise among others naringin dihydrochalcone and/or neohesperidin dihydrochalcone.

The object of the present invention was therefore to provide a method by means of which flavanone glycosides can be converted quickly and in high yields by biotechnological methods to the corresponding dihydrochalcones, wherein chemical intermediate steps should be avoided completely.

DESCRIPTION OF THE INVENTION

Figure 1:
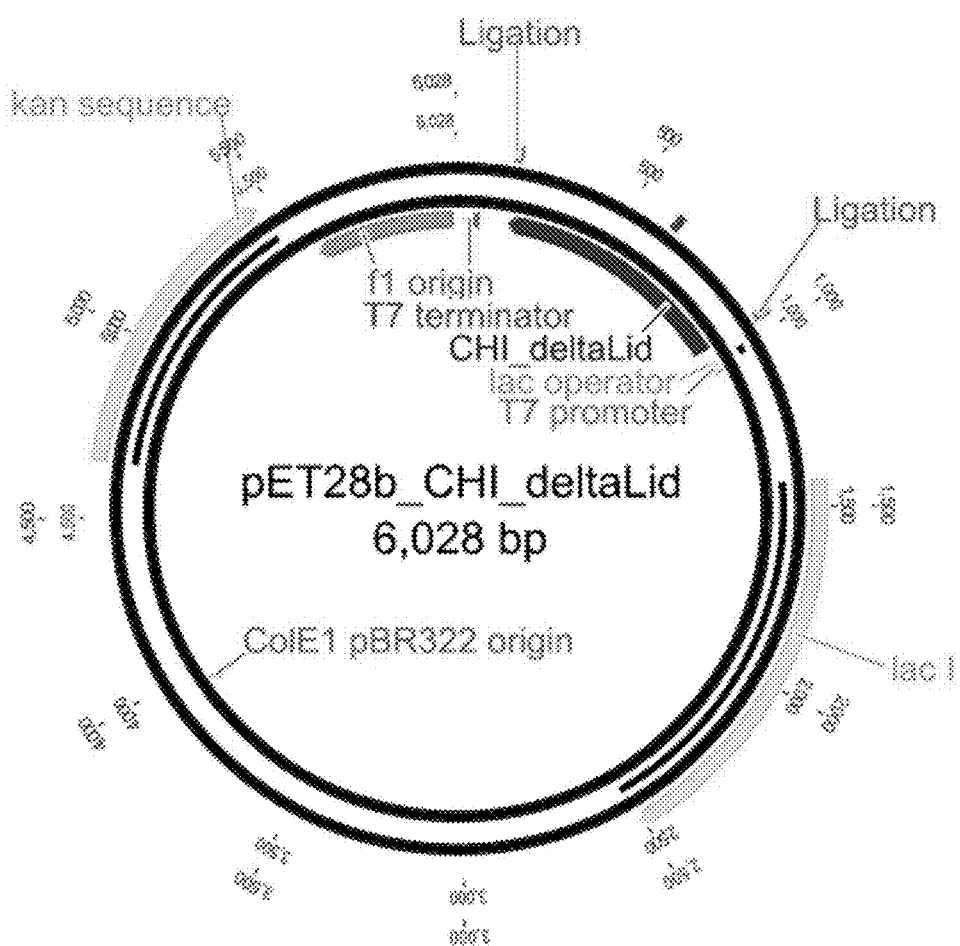
FIG. 1 is a depiction of Plasmid pET28 CHI ΔLid.

A first subject matter of the invention relates to a process for the preparation of flavanone glycoside dihydrochalcones comprising the steps of:
(a) provision of a transgenic microorganism containing
   (i) a first nucleic acid section (A) containing a gene coding for a bacterial chalcone isomerase, and
   (Ii) a second nucleic acid section (B) containing a gene coding for a bacterial enoate reductase gene
   wherein the nucleic acid section (A)
   (1) represents a nucleotide sequence according to SEQ ID NO: 1, in which the nucleic acid section (A') according to SEQ ID NO: 3 has been cut out, or
   (2) codes for an amino acid sequence according to SEQ ID NO:2, in which the amino acid section (A') according to SEQ ID NO:4 has been cut out,
(b) addition of one or more flavanone glycosides to the transgenic microorganism,
(c) culturing the transgenic microorganism under conditions which allow the simultaneous isomerisation and reduction of the flavanone glycoside to the flavanone glycoside dihydrochalcone, and optionally,
(d) isolation and purification of the final product.

It has surprisingly been found that by incorporating two different nucleic acid sections, one of which contains a gene coding for a bacterial chalcone isomerase and the other of which contains a gene coding for a bacterial enoate reductase in a suitable microorganism, preferably a facultative anaerobic microorganism, a system is provided which, on the addition of flavanone glycosides and culturing, simultaneously enables the isomerisation of the flavanone glycoside to the chalcone and the reduction of the chalcone to the dihydrochalcone in short times and excellent yields, as illustrated by the example of the reaction of the flavanone glycoside naringin to naringin dihydrochalcone:

of the class Clostridia, in particular of the order Clostridiales, wherein of these the anaerobic organism *Eubacterium ramulus* is particularly preferred.

Particularly preferred or the purposes of the present invention is the use of a chalcone isomerase which has one, several or all of the following properties:

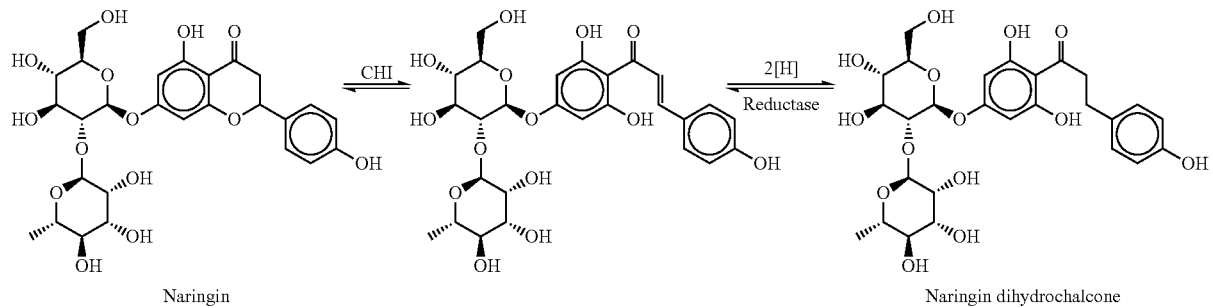

Since the whole procedure takes place only by enzymatic/fermentation processes, the thereby obtained flavanone glycoside dihydrochalcones may be described as natural.

Chalcone Isomerases

A "chalcone isomerase" (CHI) in the sense of the present invention is an enzyme that catalyses the reaction of a flavanone to the chalcone. In particular the CHI catalyses the reaction of naringin to naringin chalcone.

In a specific embodiment of the invention the present biotechnological method is characterised in that a bacterial chalcone isomerase in combination with a bacterial enoate reductase, preferably of the same bacterium, is introduced into a transgenic microorganism, which is then capable of forming the desired flavanone glycoside dihydrochalcones, in particular naringin dihydrochalcone.

For this purpose, firstly and in particular a bacterial chalcone isomerase comes into question, which is derived from a microorganism of the phylum Firmicutes, preferably

| $K_M$ [µmol/l] | $V_{max}$ [U/mg] | $K_{cat}$ [s$^{-1}$] | $K_{cat}/k_M$ [l * mol$^{-1}$ * s$^{-1}$] |
|---|---|---|---|
| 36.83 | 107.3 | 416.7 | 1.13 * 10$^7$ |

From the prior art it is known that the anaerobic microorganism *Eubacterium ramulus* is able to degrade naringenin, whereby phloretin is formed as an intermediate. In *Eubacterium ramulus*, phloretin formed as an intermediate is directly metabolised (see Schneider et al, Anaerobic degradation of flavonoids by *Eubacterium ramulus*, Arch. Microbiol (2000). 173: 71-75), as shown in the following reaction scheme (see in particular the reaction mediated by phloretin hydrolase (PhH):

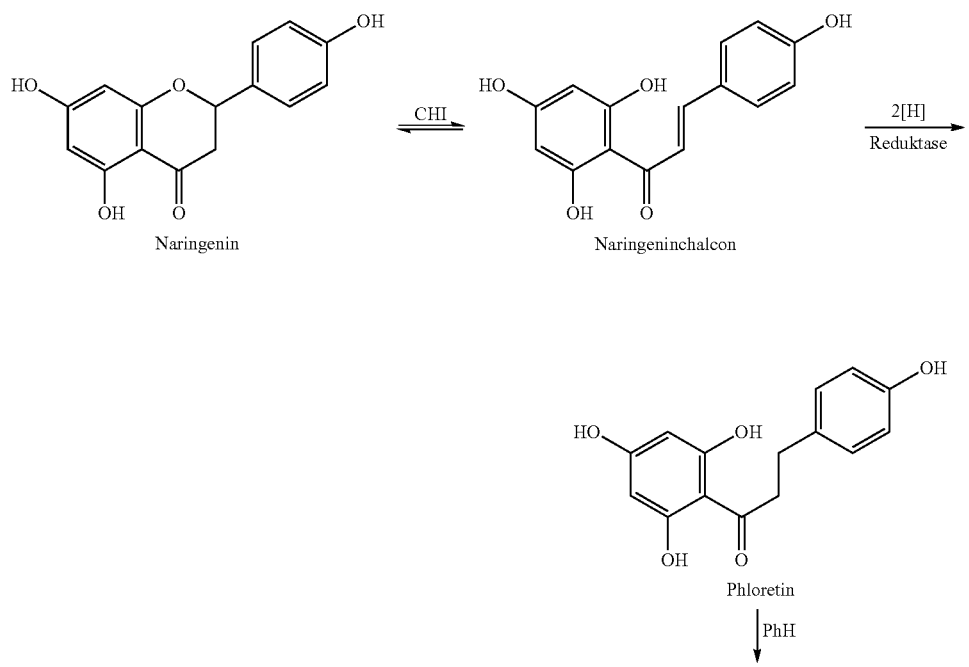

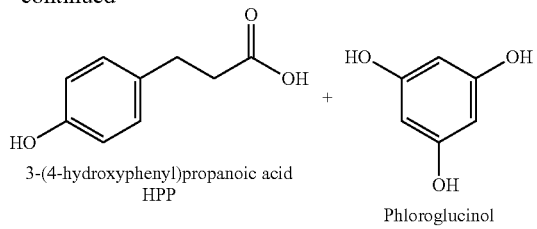

3-(4-hydroxyphenyl)propanoic acid
HPP

Phloroglucinol

Various possible applications of enzyme systems and methods of microbial biotransformation are described in the prior art; for example, the possibility of a simple reduction of double bonds by means of yeasts (such as *Saccharomyces*) is known. Enzymatic cleavages of ethers have hitherto hardly been studied.

In connection with the present invention reference is principally made to the following publications: Schoefer et al, Anaerobic degradation of flavonoids by *Clostridium orbiscindens*, Appl. Environ. Microbiol., October 2003, p. 5849-5854; and Herles et al, "First bacterial chalcone isomerase isolated from *Eubacterium ramulus*" Arch Microbiol (2004) 181: 428-434. Discoveries relating to the degradation of lignin have been described for example by Masai et al. (Masai et al., 1993; Otsuka et al., 2003; see also. JP 2002034557).

In WO 2006 010117 A1 (KOFFAS) and WO 2005 084305 A1 (SCHMIDT-DANERT) the use of heterologous expression for the formation of flavonoids is described. There, (exclusively) plant genes are described, and various substances for a heterologous expression of different substances are disclosed (starting from L-phenylalanine, tyrosine and cinnamic acid).

In connection with the present invention it was however found that chalcone isomerases in general and the CHI example *E. ramulus* do not always exhibit satisfactory product yields if the corresponding glycosides are used instead of the aglycones. A particular aspect of the present invention was thus effecting specific modifications to the enzyme, such that now aglycones or the corresponding glycosides can be used in practically the same way and the corresponding dihydrochalcones are then also expressed in a short time and in satisfactory yields.

A preferred embodiment of the present invention relates to a process which is characterised in that the nucleic acid section (A) introduced into the transgenic microorganism contains a nucleotide sequence according to SEQ ID NO: 1, in which the nucleic acid section (A') according to SEQ ID NO: 3 has been cut out.

In principle, also suitable are those nucleic acid sections that are at least 50%, preferably at least 60% and especially at least 80% identical to the nucleic acid sections (A-A') according to the invention, even the same advantageous expression times and expression yields cannot be achieved with these sequences.

Mutatis mutandis, a method in which the bacterial chalcone isomerase contains a nucleotide sequence according to SEQ ID NO: 1, in which the nucleic acid section (A') according to SEQ ID NO: 3 has been cut out, is also a subject matter of the invention.

The present invention further relates to a process which is characterised in that the amino acid section (A) expressed in the transgenic microorganism contains an amino acid sequence according to SEQ ID NO: 2, in which the amino acid section (A') according to SEQ ID NO: 4 has been cut out.

In principle, also suitable are those amino acid sections that are at least 50%, preferably at least 60% and especially at least 80% identical to the amino acid sequences (A-A') according to the invention, even if the same advantageous expression times and expression yields cannot be achieved with these sequences.

Mutatis mutandis, also the subject matter of the invention is a process in which the bacterial chalcone isomerase contains an amino acid sequence according to SEQ ID NO: 2, in which the amino acid section (A') according to SEQ ID NO: 4 has been cut out.

In the context of the present invention the "amino acid sequence identity" should preferably be determined with the aid of the Waterman-Smith algorithm with a gap open penalty of 10, a gap extension penalty of 0.5 and the BLOSUM62 matrix (with regard to the Waterman-Smith algorithm, see for example Smith, T. F. and Waterman, M. S., "Identification of common molecular sub-sequences", Journal of Molecular biology (1981) 147: 195-197; implemented online via the corresponding tool side of the EMBL). The submitted nucleotide sequences were generated using the software BISSAP of the European Patent Office according to WIPO Standard 25.

The removal of the said section from the overall sequence may be carried out for example with the FastCloning method. For this purpose a PCR is performed with the following primers:

Forward primer: 5'-GATCCCGGCAGCAGCAGAAGGAAATCC-3'

Reverse primer: 5'-GGATTTCCTTCTGCTGCTGCCGGGATC-3'

The output plasmid is then digested with DpnI. After successful cloning the plasmid pET28_CHI_ΔLid that is thereby obtained can be transformed together with the second plasmid pET22_ERED (as explained in more detail hereinafter) into a microorganism, here preferably *E. coli* BL21, in a manner known per se.

Enoate Reductases

An "enoate reductase" (ERED) in the sense of the present invention is an enzyme which catalyses the dehydrogenation of certain compounds, in particular the reaction of naringenin glycoside chalcone to form naringenin glycoside dihydrochalcone.

As a second and also preferred embodiment is a bacterial enoate reductase obtained from a microorganism of the phylum Firmicutes, preferably of the class Clostridia, in particular of the order Clostridiales, among which the anaerobic organism *Eubacterium ramulus* is particularly preferred. Preferred overall is the double transformation of both the chalcone isomerase and the enoate reductase from *Eubacterium ramulus* in a suitable microorganism, preferably E. coli. For the purposes of the present invention the use of an enoate reductase having a protein size of 74.455 kDa and/or expressed in both the soluble and in the insoluble protein fraction after up to 20 h under anoxic conditions at various temperatures, is preferred.

A further particular embodiment of the invention therefore relates to a process which is characterised in that the nucleic acid section (B) introduced into the transgenic microorganism is a nucleotide sequence according to SEQ ID NO: 5 or SEQ ID NO. 7.

Mutatis mutandis, also the subject matter of the invention is a process in which the bacterial enoate reductase contains a nucleotide sequence of SEQ ID NO: 5 or SEQ ID NO:7.

A further particular embodiment of the invention therefore relates to a process which is characterised in that the amino acid section (B) expressed in the transgenic microorganism is an amino acid sequence according to SEQ ID NO: 6.

In principle, also suitable are those amino acid sections that agree at least 50%, preferably at least 60% and especially at least 80% with the amino acid sections (B) according to the invention, even if the same advantageous expression times and expression yields cannot be achieved with these sequences.

Mutatis mutandis, also the subject matter of the invention is a process in which the bacterial enoate reductase contains an amino acid sequence according to SEQ ID NO: 6.

Flavanone Glycosides

In the context of the present invention the following substances are suitable as flavanone glycosides that are to be converted into the corresponding flavanone glycoside dihydrochalcones:

Naringin, narirutin, prunin (naringin-7-O-glucoside), hesperidin, neohesperidin, hesperetin-7-O-glucoside, eriodictyol glycosides such as eriocitrin, neoeriocitrin, eriodictyol-7-O-glucoside, homoeriodictyol glycosides such as homoeriodictyol-7-O-glucoside, sterubin glycoside, sakuranetin glycoside, isosakuranetin glycoside, 4',7-dihydroxyflavanone glycosides, 4',7-dihydroxy-3'-methoxy-flavanone glycoside, 3',7-dihydroxy-4'-methoxy-flavanone glycoside, 3',4',7-trihydroxy-flavanone glycoside, wherein with respect to the 2-position of the flavanone backbone the flavanones may be present as (S) enantiomer, as (R) enantiomer, as a racemate or as an arbitrary mixture of the two enantiomers. Some of the preferably used flavanones are shown as examples below:

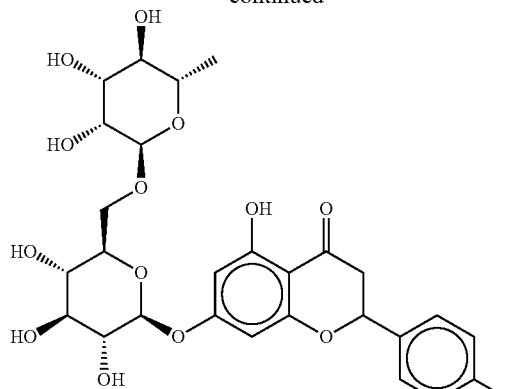

Narirutin

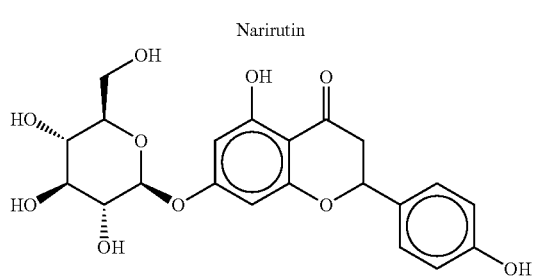

Prunin

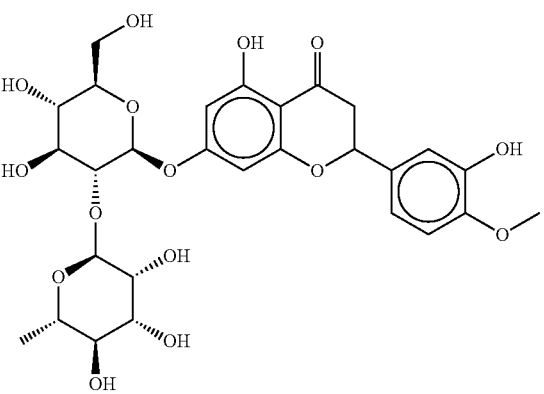

Neohesperidin

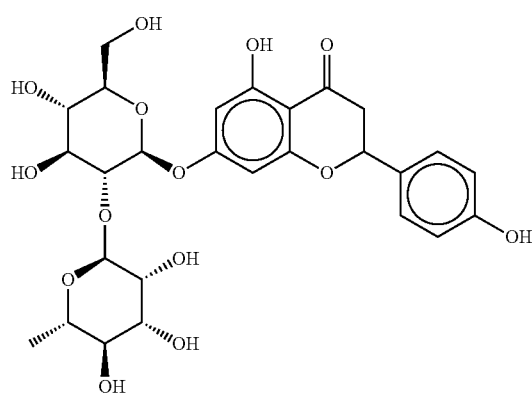

Naringin

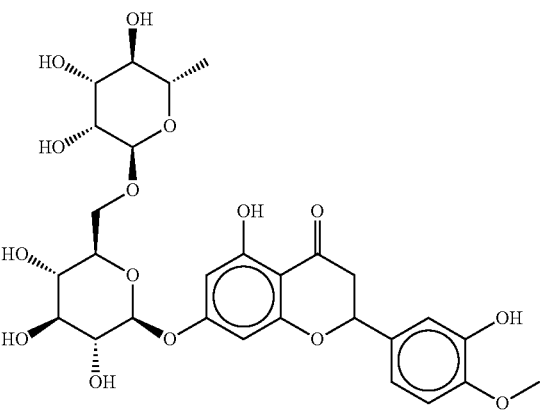

Hesperidin

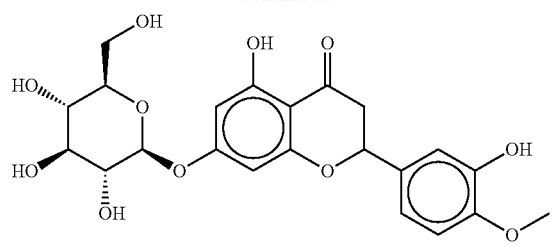
Hesperetin-7-O-glucosid
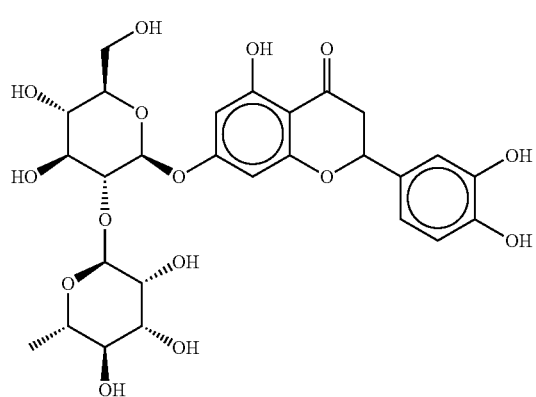
Neoeriocitrin
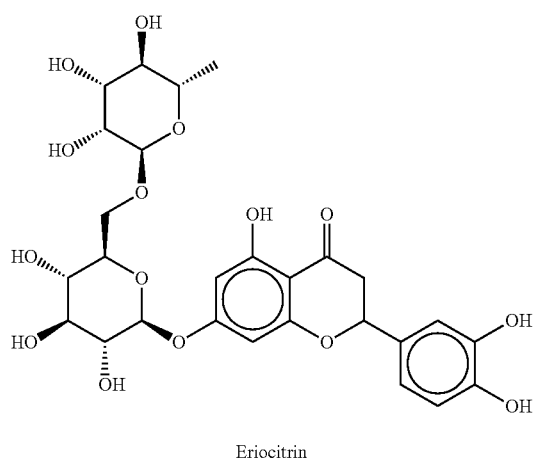
Eriocitrin
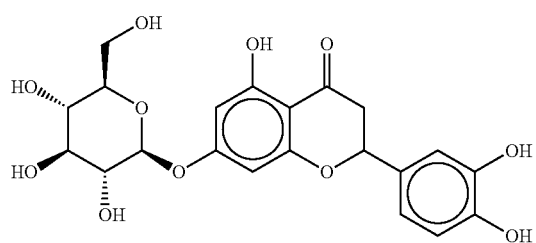
Eriodictyol-7-O-glucosid
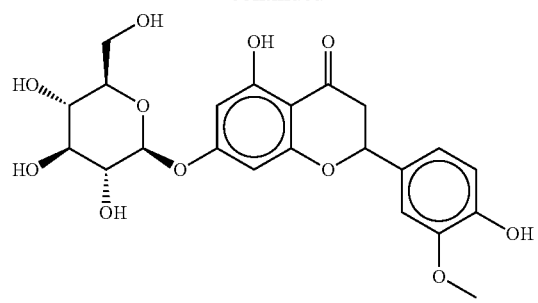
Homoeriodictyol-7-O-glucosid
These can be converted according to the method of the invention into the corresponding dihydrochalcones, which are shown below:
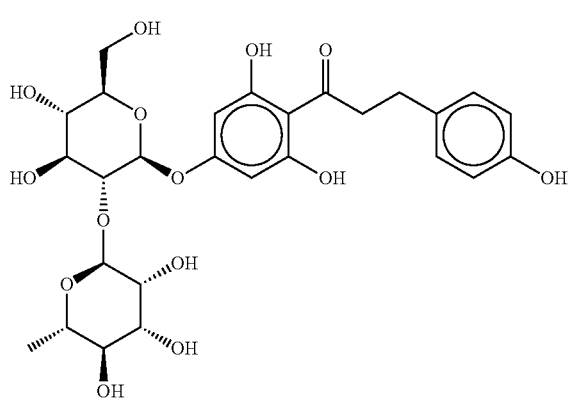
Naringindihydrochalkon
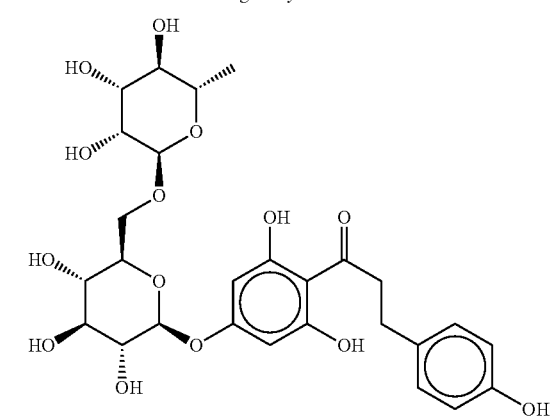
Narirutindihydrochalkon
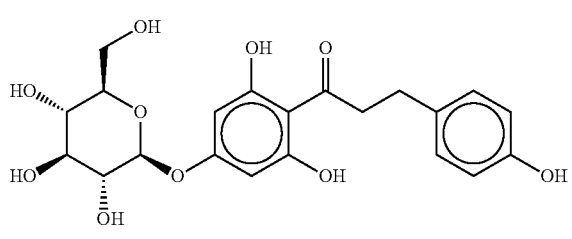
Prunindihydrochalkon = Tritobatin -continued

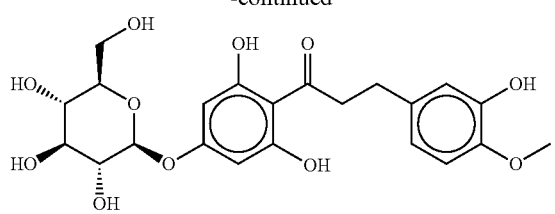

Hesperetin-7-glucosid-dihydrochalkon

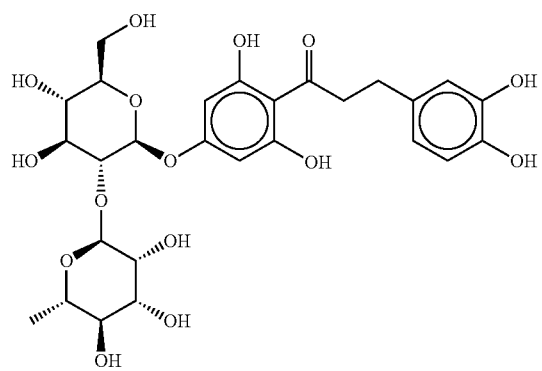

Neoeriocitrindihydrochalkon

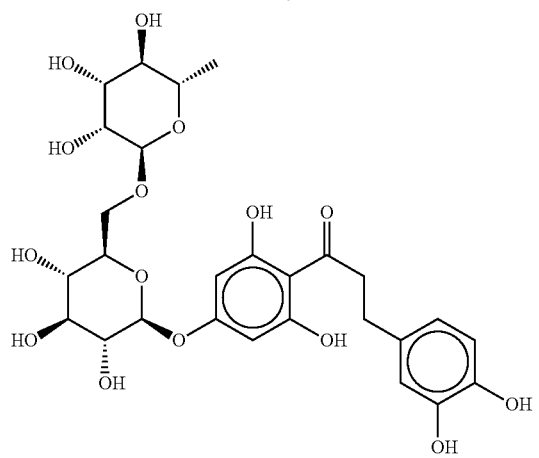

Eriocitrindihydrochalkon

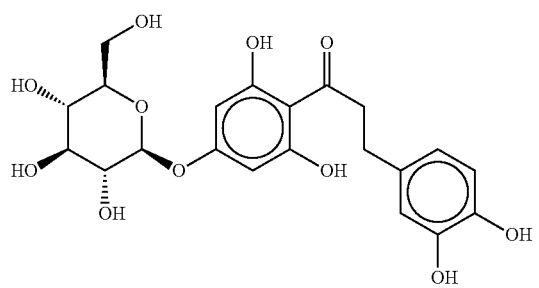

Eriodictyol-7-O-glucosid-dihydrochalkon

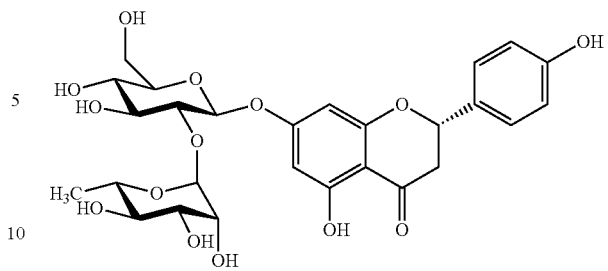

Naringin

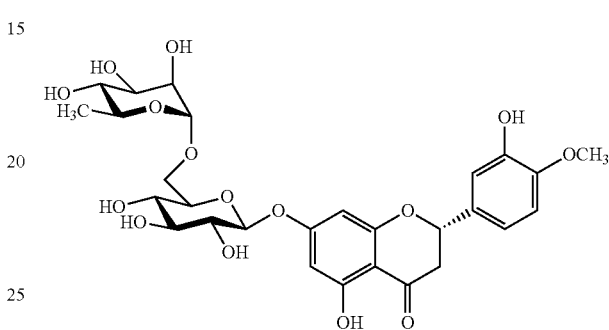

Hesperidin

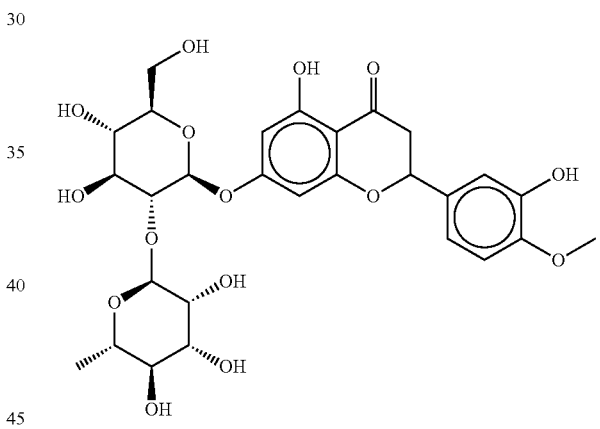

Neohesperidin

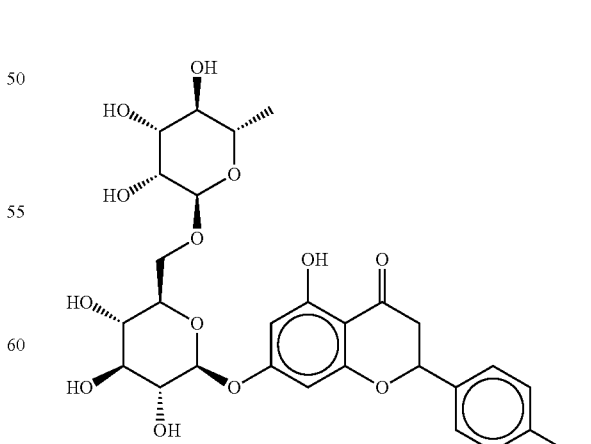

Narirutin

Particularly preferred—since it is commercially of considerable importance and can be implemented in very short times and with high yields—is the conversion of the following flavanone glycosides to the corresponding dihydrochalcones:

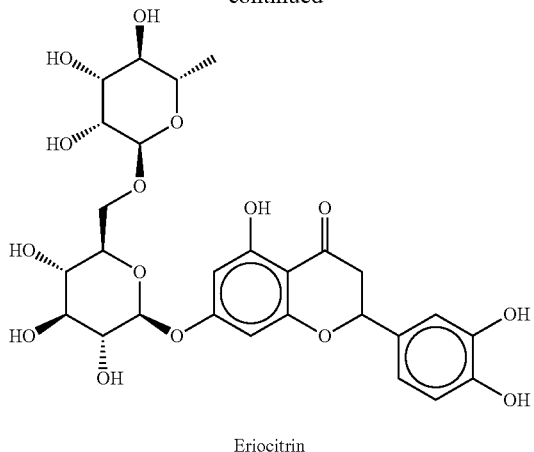

Eriocitrin

Cultivation; Expression and Isolation

As described above, in step (ii) of a process according to the invention one or more flavanone glycosides is/are added to the transgenic microorganism, wherein the transgenic microorganism is cultured under conditions that allow the conversion of the flavanone glycoside(s).

According to a preferred implementation of a process according to the invention the transgenic microorganisms are first of all, i.e. before step (ii), cultured under aerobic conditions, preferably until a maximum biomass concentration is reached. In this connection the $OD_{600}$ should preferably be at least in the range from 1 to 15 or higher, preferably in the range from 5 to 300, in particular in the range from 10 to 275, preferably in the range from 15 to 250. The microorganisms are then cultured in step (ii) preferably under anaerobic conditions, wherein the expression of the desired amino acid sequences or the desired enzymes based on the introduced nucleic acid sections or the introduced transgenes is carried out, for example excited by means of induction by IPTG and/or lactose (when using a corresponding, suitable promoter or a corresponding, suitable expression system).

In principle it is preferred according to the invention if the incubation in step (ii) takes place at least partially or completely under anaerobic conditions.

Depending on the microorganism the person skilled in the art can create in step (ii) suitable environment conditions for the purposes of the present invention and in particular can provide a suitable (cultivation) medium. The cultivation is preferably carried out in LB or TB medium. Alternatively a (more complex) medium consisting of or comprising plant raw materials, in particular citrus, grapefruit and orange plants, are used. The cultivation is carried out for example at a temperature of more than 20° C., preferably more than 25° C., in particular more than 30° C. (preferably in the range from 30 to 40° C.), which in particular favours the formation of naringin dihydrochalcone and can increase the yield. Furthermore, a temperature for the induction (see above) of less than 40° C., in particular of less than 35° C. (preferably in the range from 20 to 30° C.) can favour the formation of naringin dihydrochalcone and increase the yield.

The flavanone glycosides are with reference to the (culture) medium containing the transgenic microorganisms added in step (ii) preferably in an amount of 0.1 mM to 100 mM (mmol/L), preferably 0.5 to 95 mM, particularly preferably 1 to 90 mM, to the transgenic microorganism. In this connection suitable (co)solvents can be used.

If one or more suitable inducers, for example IPTG or lactose, are used for the induction (e.g. of the lac operon), it is preferred to use the inductor with regard to the (culture) medium that contains the transgenic microorganisms in step (ii) in an amount of 0.001 to 1 mM, preferably of 0.005 to 0.9 mM, particularly preferably of 0.01 to 0.8 mM, since particularly good yields can be achieved in this way.

To isolate or purify the expressed flavanone glycoside dihydrochalcones, extractions with organic solvents can for example be carried out. These solvents are preferably selected from the following list: isobutane, 2-propanol, toluene, methyl acetate, 2-butanol, hexane, 1-propanol, light petroleum, 1,1,1,2-tetrafluoroethane, methanol, propane, 1-butanol, butane, ethyl methyl ketone, ethyl acetate, diethyl ether, ethanol, dibutyl ether, $CO_2$, tert. butyl methyl ether, acetone, dichloromethane and $N_2O$. Particularly preferred are those solvents which form a visually recognisable phase boundary with water. After this a removal of the residual water in the solvent as well as the removal of the solvent itself can be carried out, which in turn can be followed by re-dissolving the dihydrochalcone in a (possibly different) solvent, which for example is suitable for an optionally subsequent crystallisation and drying of the product. Alternatively or in addition an adsorptive, distillative and/or chromatographic purification can be carried out.

Alternatively, drying methods can be used for the isolation or purification of the formed flavanone glycoside dihydrochalcones, in particular vacuum belt drying, spray drying, distillation or lyophilisation of the cell-containing or cell-free fermentation solution may be used.

Transgenic Microorganisms

A "transgenic microorganism" is in connection with the present invention meant to be a genetically engineered or modified microorganism, in which nucleic acid sections (see nucleic acid sections (A) and (B) as described herein) or genes of another organism (so-called. transgenes) have been introduced in a targeted manner by means of biotechnological methods.

A further subject matter of the invention therefore comprises a transgenic microorganism containing (i) a first nucleic acid section (A) containing a gene coding for a bacterial chalcone isomerase, and (ii) a second nucleic acid section (B) containing a gene coding for a bacterial enoate reductase, wherein the nucleic acid section (A)

(1) represents a nucleotide sequence according to SEQ ID NO: 1, in which the nucleic acid section (A') according to SEQ ID NO: 3 has been cut out, or (2) represents an amino acid sequence according to SEQ ID NO:2, in which the amino acid section (A') according to SEQ ID NO: 4 has been cut out.

Preferably this is a facultative anaerobic microorganism, preferably a proteobacterium, in particular an enterobacterium, for example of the genus *Escherichia*, preferably *E. coli*, especially *E. coli* Rosetta, *E. coli* BL21 *E. coli* K12, *E. coli* MG1655 *E. coli* SE1 and their derivatives, yeasts, for example *S. cerevisiae* and *P. pastoris, K. lactis, H. polymorpha* and also fungi such as *Aspergillus* spp. or *Trichoderma* spp.

The transgenic microorganism according to the invention is characterised in particular by the fact that (i) the gene coding for a bacterial chalcone isomerase codes for a chalcone isomerase from a microorganism from the phylum Firmicutes, and/or (ii) the gene coding for a bacterial enoate reductase codes for an enoate reductase from a microorganism from the phylum Firmicutes.

Methods that allow on the basis of the introduced nucleic acid sections and the transgenes an expression of the desired amino acid sequences or the desired enzymes, are also sufficiently well known to the person skilled in the art, for example using a regulatory element, in particular a promoter.

Vector

Another aspect of the present invention relates to a vector, i.e. a transport vesicle ("gene shuttle") for transferring foreign nucleic acid(s) into a recipient cell, in particular a plasmid vector, that allows the cloning of one or more nucleic acid sections, containing (i) a first nucleic acid section (A) containing a gene coding for a bacterial chalcone isomerase, and (ii) a second nucleic acid section (B) containing a gene coding for a bacterial enoate reductase, wherein the nucleic acid section (A)

(1) represents a nucleotide sequence according to SEQ ID NO: 1, in which the nucleic acid section (A') according to SEQ ID NO: 3 has been cut out, or (2) represents an amino acid sequence according to SEQ ID NO:2, in which the amino acid section (A') according to SEQ ID NO:4 has been cut out.

The invention further comprises a vector, preferably a plasmid vector, which is characterized in that it has (i) a first nucleic acid sequence (A), containing a gene coding for a bacterial chalcone isomerase, and (ii) a second nucleic acid section (B) containing a gene coding for a bacterial enoate reductase, wherein the nucleic acid section (A)

(1) represents a nucleotide sequence according to SEQ ID NO: 1, in which the nucleic acid section (A') according to SEQ ID NO: 3 has been cut out, or (2) represents an amino acid sequence according to SEQ ID NO:2, in which the amino acid section (A') according to SEQ ID NO:4 has been cut out.

Host Cell

The present invention also relates to a host cell containing one or more identical or different vectors according to the invention as described herein. According to the invention a host cell is preferred that contains one or more vectors with a nucleic acid section (A) containing a gene coding for a bacterial chalcone isomerase, and also contains one or more vectors with a nucleic acid section (B) containing a gene coding for a bacterial enoate reductase.

A host cell according to the invention is preferably a microorganism used according to the invention or a microorganism according to the invention (as described above). The host cells according to the invention described herein and/or the microorganisms according to the invention or used according to the invention are or serve preferably as (production) strain for the biotechnological production of dihydrochalcones described herein, in particular naringin dihydrochalcone.

Preparations

Using the process according to the invention one or more of the above mentioned flavanone glycosides, which are contained in flavanone glycoside-containing foods or preparations suitable for food production, can be converted into the corresponding dihydrochalcones and are thus recognised as natural preparations, which are characterised in that they contain at least one of the above mentioned dihydrochalcones and are therefore less bitter and taste sweeter than the starting preparation.

In this connection the above-defined flavanone glycoside are preferably found in plant parts, in particular fruits or fruit preparations or products obtained by conventional processes, form example dried fruits or fresh or dried fruit parts (z. B. albedo, flavedo), fresh juices, juice fractions, secondary products of juice production, essential oils, oleoresins, juice concentrates, fruit purees, press cakes, fresh or dried leaves, of the genera *Citrus* and *Poncirus* or *Clymenia* or *Eremocitrus* or *Microcitrus* or *Oxanthera* or *Fortunella* or *Eriodictyon* or *Viscum*. The flavanone glycosides defined above can be isolated, extracted or enriched from the products obtained by conventional processes also by solvents or solvent mixtures permitted for use in food production, or by altering the pH, preferably to the alkaline range, followed by acid treatment.

The thereby obtained flavanone glycoside-containing foods or preparations suitable for food production are then converted by the processes according to the invention into dihydrochalcone glycoside-containing preparations identifiable as natural preparations, and can then be used as such or, after removal of the host cell and/or their components and optional concentration by physical processes, can be employed as a preparation suitable for food production, preferably as a preparation suitable for food production having a bitter-masking or sweetness-intensifying or effect.

Examples of suitable foods include in particular confectionery (for example chocolates, chocolate bar products, other bar products, fruit gums, hard and soft caramels, chewing gum), alcoholic or non-alcoholic beverages (e.g. coffee, tea, iced tea, wine, wine-containing beverages, beer, beer-containing beverages, liqueurs, spirits, brandies, (carbonated) fruit-containing lemonades, (carbonated) isotonic beverages, (carbonated) soft drinks, nectars, spritzers, fruit and vegetable juices, fruit or vegetable juice preparations and also instant beverages (for example instant cocoa drinks, instant tea drinks, instant coffee drinks, instant fruit drinks).

Particularly preferred in this connection as flavanone glycoside-containing foods are citrus juices, in particular orange juices, which contain a high content of naringin and can be converted by the process according to the invention into naringin dihydrochalcone-containing orange juices according to the invention.

EXAMPLES

Example 1

Cloning Strategy

The excision of the Lid sequence from the gene of CHI was performed by means of the FastCloning method. For this purpose a PCR was carried out with the primers listed below to pET28_CHI (denaturation: 30 s 95° C., annealing: 30 s 50° C., elongation: 6.5 min 72° C.). The output plasmid was then digested with Dpni.

```
Forward primer:  5'-GATCCCGGCAGCAGCAGAAGGAAATCC-3'

Reverse primer:  5'-GGATTTCCTTCTGCTGCTGCCGGGATC-3'
```

After successful cloning the plasmid pET28_CHI_ΔLid (FIG. 1) together with the plasmid pET22_ERED was transformed into *E. coli* BL21.

Example 2

Expression of the Double Transformation 200 mL $LB_{kan,\ amp}$ were inoculated with 1% (v/v) of an overnight culture and grown at 37° C. to an OD≥1. The induction of the expression was then carried out with 0.1 mM IPTG. The expression of the protein was carried out for 21 h at 20° C.

Figure 2:
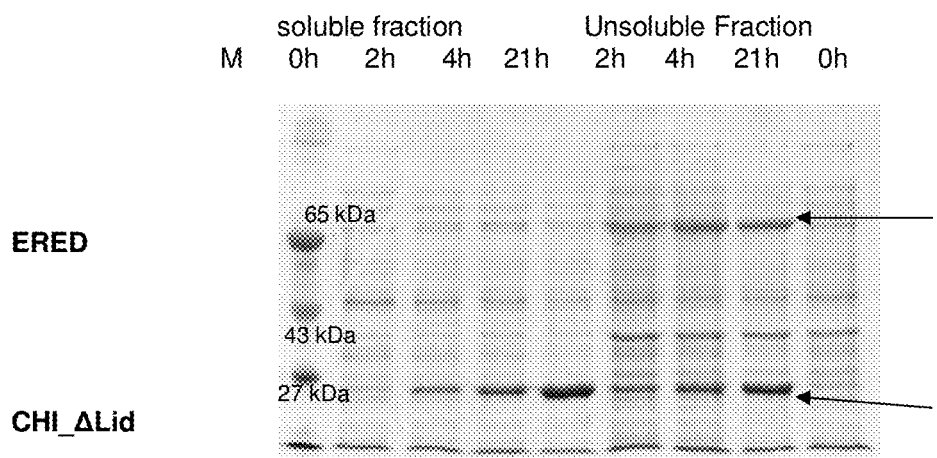
FIG. 2 illustrates the SDS-PAGE of the expression of the double transformation of pET22 ERED and pET28 CHI ΔLid, wherein 0h denotes the time point of the induction.

As can be see in FIG. 2, the expression of the CHI_ΔLid was carried out in the soluble as well as in the insoluble fraction, while the ERED is expressible only in the insoluble form.

Example 3

Whole-Cell Biocatalyses

After the harvesting of the cells these were normalised with 20 mM TRIS-HCl pH 7.5 to an OD=150. For the implementation of the biocatalyses in each case 490 μL of the cell suspension was added with 10 μL naringin solution (stock solution: 7.5 mM naringin dissolved in 1,2-propylene glycol; final concentration: 150 μM) to a 2 mL Eppendorf reaction vessel and gassed with nitrogen. The biocatalyses were carried out at 23° C., 900 rpm and 22 h. The extraction of the substrates was carried out twice with ethyl acetate.

Figure 3:
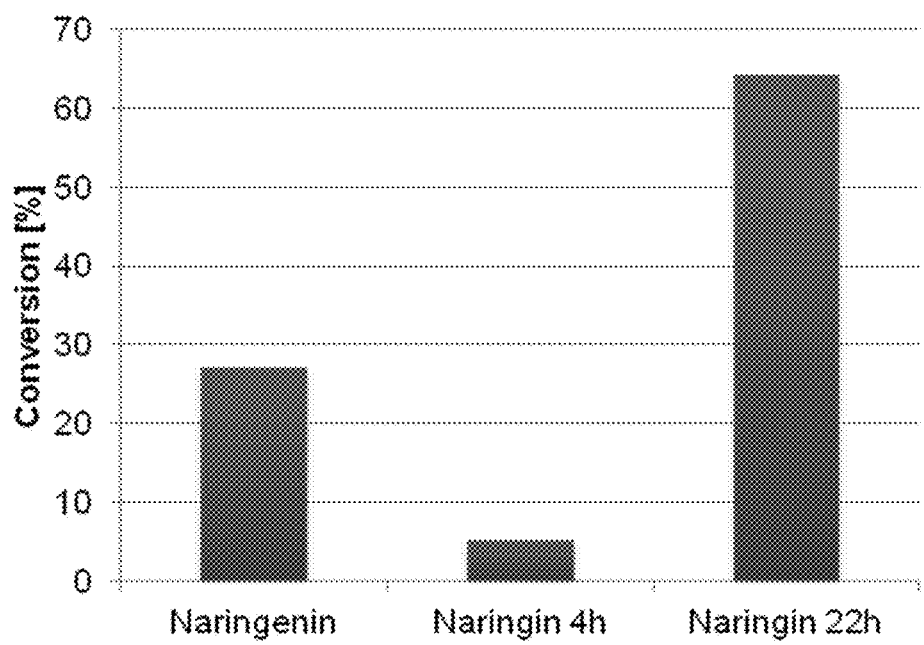
FIG. 3 shows the conversion of naringin by means of whole-cell-catalysis.

After 22 h a 65% conversion of the naringin was observed (FIG. 3).

Example 4

Debittering of Naringin-Containing Orange Juice

An orange juice with a concentration of 100 ppm naringin is incubated with the cells described in Example 3 and incubated at 23° C. for 48 hours while stirring. The content of naringin was lowered to 50 ppm and simultaneously naringin dihydrochalcone is formed.

The invention claimed is:

1. A transgenic microorganism comprising:
   (i) a first nucleic acid section (A) containing a gene coding for a bacterial chalcone isomerase, and
   (ii) a second nucleic acid section (B) containing a gene coding for a bacterial enoate reductase,
   wherein the nucleic acid section (A)
   (1) comprises a nucleotide sequence corresponding to the nucleotide sequence set forth as SEQ ID NO: 1, from which the nucleic acid section (A') according to SEQ ID NO: 3 has been deleted, or
   (2) encodes an amino acid sequence corresponding to the amino acid sequence set forth as SEQ ID NO: 2, from which the amino acid section (A') according to SEQ ID NO: 4 has been deleted.

2. The microorganism according to claim 1, wherein the microorganism is a facultative anaerobic microorganism.

3. The microorganism according to claim 1, wherein
   (i) the gene coding for a bacterial chalcone isomerase codes for a chalcone isomerase of a microorganism from the phylum of the firmicutes, and/or (ii) the gene coding for a bacterial enoate reductase codes for an enoate reductase of a microorganism from the phylum of the firmicutes.

4. A vector comprising:
(i) a first nucleic acid section (A) containing a gene coding for a bacterial chalcone isomerase, and
(ii) a second nucleic acid section (B) containing a gene coding for a bacterial enoate reductase,
wherein the nucleic acid section (A)
(1) comprises a nucleotide sequence corresponding to the nucleotide sequence set forth as SEQ ID NO: 1, from which the nucleic acid section (A') according to SEQ ID NO: 3 has been deleted, or
(2) encodes an amino acid sequence corresponding to the amino acid sequence set forth as SEQ ID NO: 2, from which the amino acid section (A') according to SEQ ID NO: 4 has been deleted.

5. The vector according to claim 4 comprising:
(i) a first nucleic acid section (A) containing a gene coding for a bacterial chalcone isomerase, and
(ii) a second nucleic acid section (B) containing a gene coding for a bacterial enoate reductase,
wherein the nucleic acid section (A)
(1) comprises a nucleotide sequence corresponding to the nucleotide sequence set forth as SEQ ID NO: 1, from which the nucleic acid section (A') according to SEQ ID NO: 3 has been deleted, or
(2) encodes an amino acid sequence corresponding to the amino acid sequence set forth as SEQ ID NO:2, from which the amino acid section (A') according to SEQ ID NO: 4 has been deleted.

6. A host cell comprising at least one vector according to claim 4.

7. A host cell comprising at least one vector according to claim 5.

8. A method for preparing flavanone glycoside dihydrochalcones comprising:
(a) providing a transgenic microorganism according to claim 1,
(b) adding one or more flavanone glycosides to the transgenic microorganism,
(c) culturing the transgenic microorganism under conditions which allow the simultaneous isomerisation and reduction of the flavanone glycoside to the flavanone glycoside dihydrochalcone, and,
(d) optionally, isolating and purifying the final product.

9. The method according to claim 8, characterized in that the transgenic microorganism is a facultative anaerobic microorganism.

10. The method according to claim 8, characterized in that the gene coding for a bacterial chalcone isomerase codes for a chalcone isomerase of a microorganism from the phylum of the firmicutes.

11. The method according to claim 8, characterized in that the gene coding for a bacterial enoate reductase codes for an enoate reductase of a microorganism from the phylum of the firmicutes.

12. The method according to claim 8, characterized in that the flavanone glycosides are selected from the group consisting of Naringin, Narirutin, Prunin (Naringin-7-O-glucoside), Hesperidin, Neohesperidin, Hesperetin-7-O-glucoside, Eriodictyol glycosides such as Eriocitrin, Neoeriocitrin, Eriodictyol-7-O-glucoside, Homoeriodictyol glycosides such as Homoeriodictyol-7-O-glucoside, Sterubin glycoside, Sakuranetin glycoside, Isosakuranetin glycoside, 4',7-dihydroxyflavanone glycosides, 4',7-dihydroxy-3'-methoxy-flavanone glycosides, 3',7-dihydroxy-4'-methoxy-flavanone glycosides, 3',4',7-trihydroxy-flavanone glycosides, and mixtures thereof.

* * * * *

UNITED STATES PATENT AND TRADEMARK OFFICE
CERTIFICATE OF CORRECTION

PATENT NO. : 10,538,797 B2
APPLICATION NO. : 15/322768
DATED : January 21, 2020
INVENTOR(S) : Maren Thomsen et al.

It is certified that error appears in the above-identified patent and that said Letters Patent is hereby corrected as shown below:

On the Title Page

(72) Inventors should read:
--Maren Thomsen, Greifswald, (DE);
Jakob Ley, Holzminden, (DE); Egon Gross, Holzminden, (DE); Winfried Hinrichs, Greifswald, (DE); Uwe Bornscheuer, Greifswald, (DE); Torsten Geissler, Einbeck, (DE)--

Signed and Sealed this
Twenty-first Day of April, 2020

Andrei Iancu
*Director of the United States Patent and Trademark Office*